US011400292B2

(12) United States Patent
Eskandar et al.

(10) Patent No.: US 11,400,292 B2
(45) Date of Patent: Aug. 2, 2022

(54) SYSTEMS AND METHODS FOR TREATING MENTAL AND NEUROLOGICAL DISORDERS INVOLVING ABNORMALLY HIGH BRAIN CONNECTIVITY

(71) Applicant: The General Hospital Corporation, Boston, MA (US)

(72) Inventors: Emad N. Eskandar, Boston, MA (US); Alik S. Widge, Boston, MA (US); Darin D. Dougherty, Boston, MA (US)

(73) Assignee: The General Hospital Corporation

( * ) Notice: Subject to any disclaimer, the term of this patent is extended or adjusted under 35 U.S.C. 154(b) by 263 days.

(21) Appl. No.: 16/468,134

(22) PCT Filed: Dec. 12, 2017

(86) PCT No.: PCT/US2017/065865
§ 371 (c)(1),
(2) Date: Jun. 10, 2019

(87) PCT Pub. No.: WO2018/111905
PCT Pub. Date: Jun. 21, 2018

(65) Prior Publication Data
US 2020/0069948 A1    Mar. 5, 2020

Related U.S. Application Data

(60) Provisional application No. 62/432,920, filed on Dec. 12, 2016.

(51) Int. Cl.
*A61N 1/36* (2006.01)
*A61N 1/05* (2006.01)

(52) U.S. Cl.
CPC ....... *A61N 1/36082* (2013.01); *A61N 1/0534* (2013.01); *A61N 1/3614* (2017.08);
(Continued)

(58) Field of Classification Search
CPC .............. A61N 1/36082; A61N 1/3614; A61N 1/0534; A61N 1/36153; A61N 1/36157; A61N 1/36171; A61N 1/36175
See application file for complete search history.

(56) References Cited

U.S. PATENT DOCUMENTS 10,406,368 B2 *  9/2019  Hershey ............ A61N 1/36017
2006/0149337 A1   7/2006  John
(Continued)

OTHER PUBLICATIONS

Bourne, Sarah Kathleen, et al. "Mechanisms of deep brain stimulation for obsessive compulsive disorder: effects upon cells and circuits." Frontiers in integrative neuroscience 6 (2012): 29. (Year: 2012).*
(Continued)

*Primary Examiner* — Lindsey G Wehrheim
(74) *Attorney, Agent, or Firm* — Quarles & Brady LLP (57) ABSTRACT

A method of using deep brain stimulation (DBS) for treating mental disorders associated with high connectivity in brain circuits, such as cortico-striato-thalamo-cortical (CSTC) circuits, is provided. The method comprises providing a first electrical signal having a first frequency to a first electrode implanted at a first location within a brain circuit and providing a second electrical signal having a second frequency to a second electrode implanted at a second location within the brain circuit. The first frequency and the second frequency are unequal.

20 Claims, 6 Drawing Sheets

(52) U.S. Cl.
CPC ..... *A61N 1/36153* (2013.01); *A61N 1/36157* (2013.01); *A61N 1/36171* (2013.01); *A61N 1/36175* (2013.01)

(56) References Cited

U.S. PATENT DOCUMENTS

| | | | |
|---|---|---|---|
| 2011/0160797 A1* | 6/2011 | Makous | A61N 1/36171 607/45 |
| 2012/0185020 A1 | 7/2012 | Simon et al. | |
| 2013/0245713 A1 | 9/2013 | Tass | |
| 2015/0005568 A1* | 1/2015 | Chib | A61N 2/006 600/9 |
| 2015/0238104 A1 | 8/2015 | Tass | |
| 2016/0089532 A1* | 3/2016 | Dou | A61N 1/36082 607/116 |
| 2016/0106982 A1* | 4/2016 | Cakmak | A61N 1/36067 607/48 |
| 2016/0175557 A1 | 6/2016 | Tass | |
| 2016/0220821 A1* | 8/2016 | O'Connell | A61N 1/36064 |
| 2016/0243364 A1 | 8/2016 | Tass | |
| 2016/0331960 A1 | 11/2016 | Katnani et al. | |
| 2017/0259068 A1 | 9/2017 | Tass et al. | |
| 2017/0333711 A1 | 11/2017 | Tass et al. | |
| 2020/0214933 A1 | 7/2020 | Tass et al. | |
| 2020/0375508 A1 | 12/2020 | Tass et al. | |

OTHER PUBLICATIONS

Eusebio et al., Effects of Low-Frequency Stimulation of the Subthalamic Nucleus on Movement in Parkinson's Disease, Experimental Neurology, 2008, 209(1):125-130.

Hamani et al., Deep Brain Stimulation for Obsessive-Compulsive Disorder: Systematic Review and Evidence-Based Guideline Sponsored by the American Society for Stereotactic and Functional Neurosurgery and the Congress of Neurological Surgeons (CNS) and Endorsed by the CNS and American Association of Neurological Surgeons, Neurosurgery, 2014, 75(4):327-333.

Sidiropoulos et al., Low-Frequency Subthalamic Nucleus Deep Brain Stimulation for Axial Symptoms in Advanced Parkinson's Disease, Journal of Neurology, 2013, 260(9):2306-2311.

PCT International Search Report and Written Opinion, PCT/US2017/065865, dated Mar. 7, 2018, 15 pages.

* cited by examiner

SYSTEMS AND METHODS FOR TREATING MENTAL AND NEUROLOGICAL DISORDERS INVOLVING ABNORMALLY HIGH BRAIN CONNECTIVITY

CROSS-REFERENCES TO RELATED APPLICATIONS

The present application is a U.S. National Stage of PCT Application No. PCT/US2017/065865 filed on Dec. 12, 2017 which claims priority to U.S. Provisional Patent Application No. 62/432,920, filed Dec. 12, 2016, entitled "Method of Treating Mental and Neurological Disorders Involving Abnormally High Brain Connectivity," which is hereby incorporated by reference in its entirety.

STATEMENT REGARDING FEDERALLY SPONSORED RESEARCH

This invention was made with government support under NIH UH3 NS100548-01 and DARPA W911NF-14-2-0045, awarded by the National Institutes of Health and the Defense Advanced Research Projects Agency. The government has certain rights in the invention.

BACKGROUND

Obsessive-compulsive disorder (OCD) is a severe, chronic condition that afflicts 2-3% of the U.S. population, which equates to between 4-7 million people. OCD patients experience recurrent upsetting thoughts, such as fears of contamination, sensations of doubt, or intrusive violent thoughts. OCD patients engage in rituals such as washing, checking, and counting in response to OCD-induced anxiety. Roughly ⅓ of OCD patients are unable to work due to their symptoms, which cause life-impairing stress.

The prevailing theory of OCD is that anxiety and compulsions arise from aberrant activity in cortico-striato-thalamo-cortical (CSTC) circuits in the brain. High connectivity in the small, highly connected networks, called "loops," has been found to cause several brain disorders. Structures within the loop can get stuck in positive feedback, repeatedly exciting each other to the point that other relevant brain activity is blocked or diminished, impairing patients' function. This abnormally high, recurrent connectivity, in a variety of different circuits, is believed to be a mechanism of OCD, Parkinson disease, anxiety, depression, and fear/trauma-related disorders like post-traumatic stress disorder (PTSD). Each of these mental disorders is characterized by getting stuck in thoughts and behavior patterns that inhibit normal cognitive function. Specifically, functional MRI (fMRI) studies have confirmed the existence of increased CSTC loop connectivity in patients experiencing OCD.

Medication and behavioral therapy have been used to treat OCD, but have proven to be less effective than desired. Despite significant progress in OCD treatments in the last decade, both medication and therapy techniques have resulted in roughly 50% of patients still experiencing residual symptoms. Low success rates have created a need for alternative systems and methods for treating OCD.

Device-based treatments, like deep brain stimulation (DBS), have been developed and show both promise and limitations. DBS involves implanting a lead into a target site of a patient's brain, then passing electrical pulses through the lead to interfere with the neural activity taking place at the target site. While DBS has shown a slightly improved response rate (i.e., a decrease in Yale-Brown Obsessive Compulsive Scale score (YBOCS) greater than 35%) of around 60%, many of these responses still leave patients with serious, disabling symptoms. Patients experiencing severe OCD may experience slight improvements in mental condition, but may still be unable to work or go to school. Because DBS is more expensive and invasive than medication or therapy, DBS is considered a "last resort" therapy for OCD. Accordingly, stronger and more reliable OCD relief systems and methods are needed.

BRIEF SUMMARY

The present disclosure provides systems and methods for treating OCD and other mental disorders associated with high connectivity using circuit de-synchronization techniques to interrupt and break connectivity within CSTC or other brain circuits. Stimulating electrodes are implanted into the brain at two separate points within a single brain circuit and are provided with mismatched frequencies. The mismatched frequencies destroy synchronous neural firing within the loops, and can enable normal brain functioning.

In one aspect, the present disclosure provides a method of using deep brain stimulation (DBS) for treating mental disorders associated with high connectivity in brain circuits. The method comprises providing a first electrical signal having a first frequency to a first electrode implanted at a first location within a brain circuit. The method further comprises providing a second electrical signal having a second frequency to a second electrode implanted at a second location within the brain circuit. The first frequency and the second frequency are unequal.

In another aspect, the present disclosure provides an apparatus for treating mental and neurological disorders associated with high brain connectivity. The apparatus comprises a first electrode configured to be placed at a first location within a brain circuit, and a second electrode configured to be placed at a second location within the brain circuit. The apparatus further includes a signal generator electrically coupled to the first electrode. The signal generator is configured to generate a first signal at a first frequency and communicate the first signal to the first electrode, and generate a second signal at a second frequency and communicate the second signal to the second electrode. The first frequency and the second frequency differ by at least one Hertz.

In another aspect, the present disclosure provides a method of disrupting over-connected brain circuits within a brain using deep brain stimulation (DBS). The method comprises providing a first electrical signal to a first electrode and a second electrical signal to a second electrode. The first electrode and the second electrode are each positioned at separate locations within a common brain circuit. The first electrode and the second electrode have mismatched frequencies.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

Corresponding reference characters indicate corresponding parts throughout the several views. Although the drawings represent embodiments of the present disclosure, the drawings are not necessarily to scale and certain features may be exaggerated in order to better illustrate and explain the embodiments of the present disclosure.

DETAILED DESCRIPTION

The invention will now be described more specifically with reference to the following non-limiting examples. It is to be noted that the following examples are presented herein for purpose of illustration and description only. It is not intended to be exhaustive or to be limited to the precise form disclosed.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Generally, the present disclosure provides systems and methods of treating OCD and other mental disorders using simultaneous striatal and cortical intervention and monitoring. More specifically, the present disclosure interrupts CSTC loops by delivering mismatched frequencies to the striatal and cortical areas of the brain.

Figure 1A:
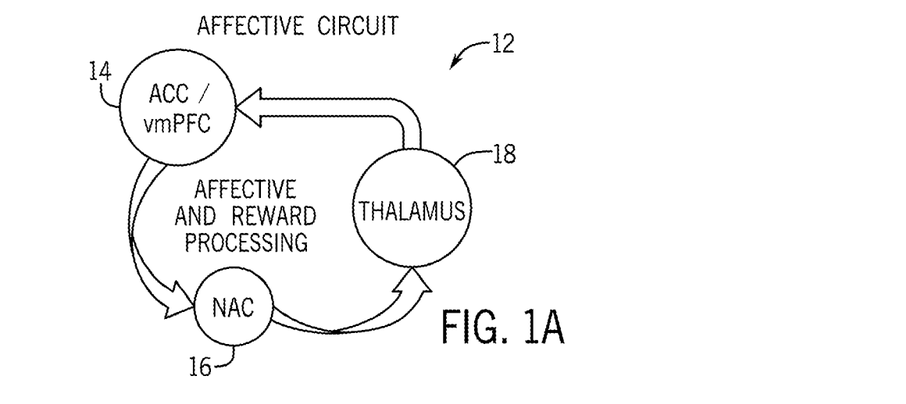
FIG. 1A is a schematic view of an affective cortico-striato-thalamo-cortical circuit contributing to OCD, demonstrating the affective circuit from the prefrontal cortex to the nucleus accumbens, to the thalamus, and back.
Figure 1B:
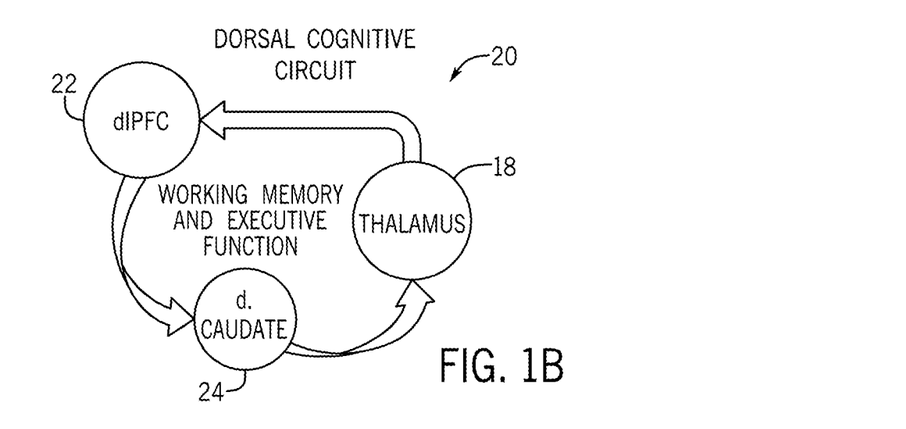
FIG. 1B is a schematic view of a second cortico-striato-thalamo-cortical circuit demonstrating the link between the dorsolateral prefrontal cortex (dlPFC) to the caudate nucleus, to the thalamus, and back to the dlPFC.
Figure 1C:
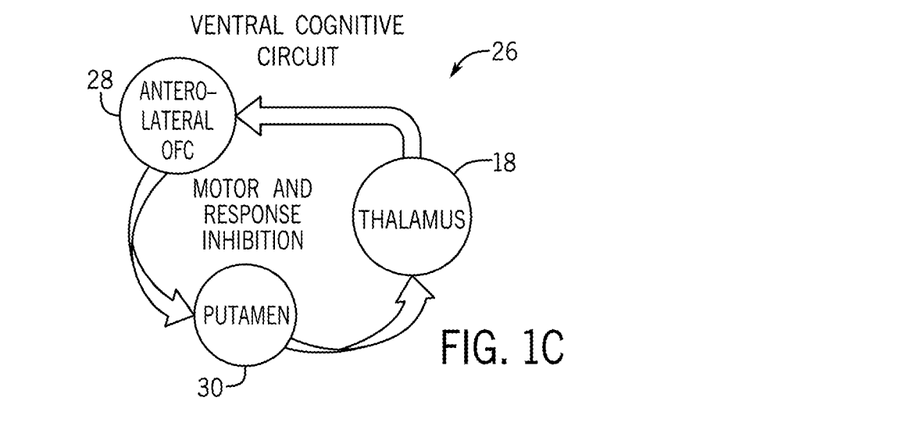
FIG. 1C is a schematic view of a third cortico-striato-thalamo-cortical circuit demonstrating the link between the anterolateral orbitofrontal cortex, the putamen, and the thalamus.
Figure 2:
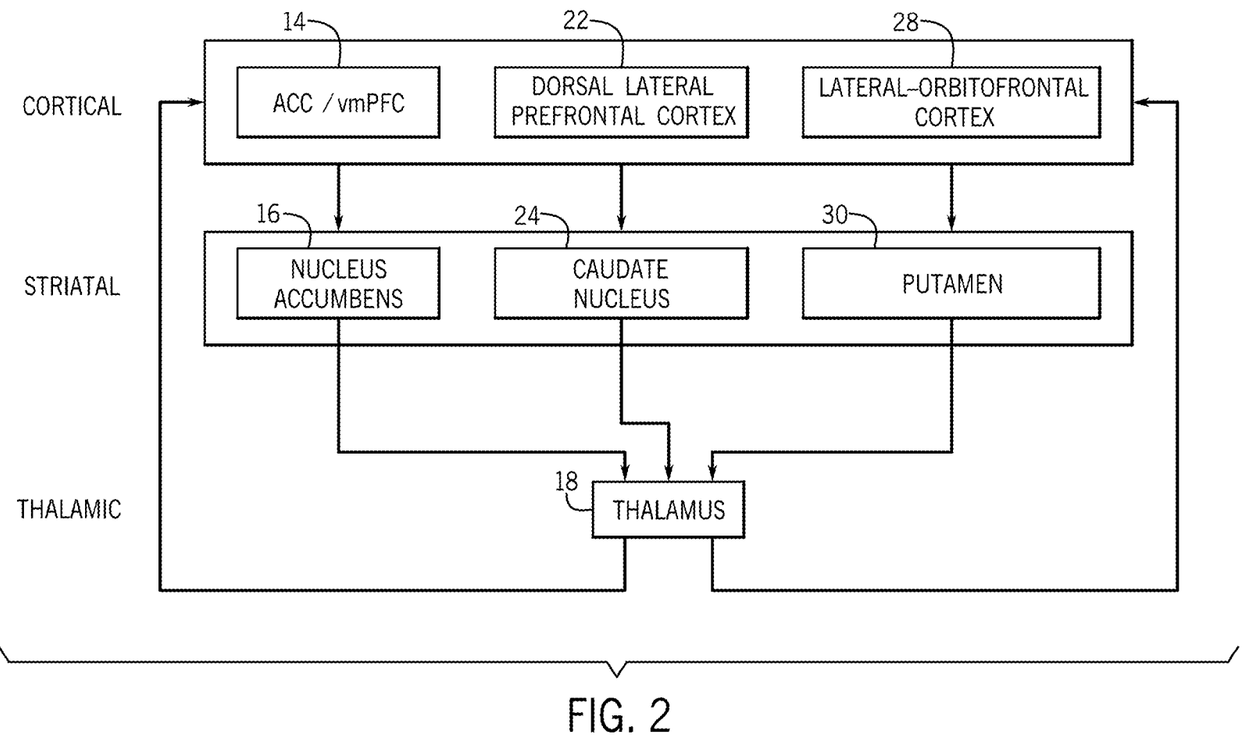
FIG. 2 is a schematic view of a cortico-striato-thalamo-cortical circuit demonstrating looping between different parts of the brain.

Referring to FIGS. 1A-4B, different types of CSTC circuits formed within the brain 10 of a patient are shown. FIG. 1A illustrates a circuit 12 that can be characterized as an affective circuit in the brain 10. The affective circuit 12 links the anterior cingulate cortex (ACC) and the ventromedial prefrontal cortex (vmPFC) 14 to the nucleus accumbens (NAc) 16, which are both connected to the thalamus 18. The affective circuit 12 can control reward processing and emotional function within the brain 10. Similar circuit structure is shown in FIG. 1B, where a dorsal cognitive circuit 20 is formed between the dorsolateral prefrontal cortex (dlPFC) 22, the dorsal caudate nucleus 24, and the thalamus 18. The dorsal cognitive circuit 20 can affect memory and executive functions of the brain 10. A ventral cognitive circuit 26 is shown in FIG. 1C, which controls motor and response inhibition. The anterolateral orbitofrontal cortex 28 passes information to the putamen 30, which again transfers information to the thalamus 18. As can be seen in each of the circuits 12, 20, 26 shown in FIGS. 1A-1C, the thalamus 18 provides feedback to each circuit 12, 20, 26, and is in communication with a portion of the cortex of the brain 10. As shown in FIG. 2, each of the circuits 12, 20, 26 exhibit connectivity between the cortex, the striatum, and the thalamus.

Figure 3:
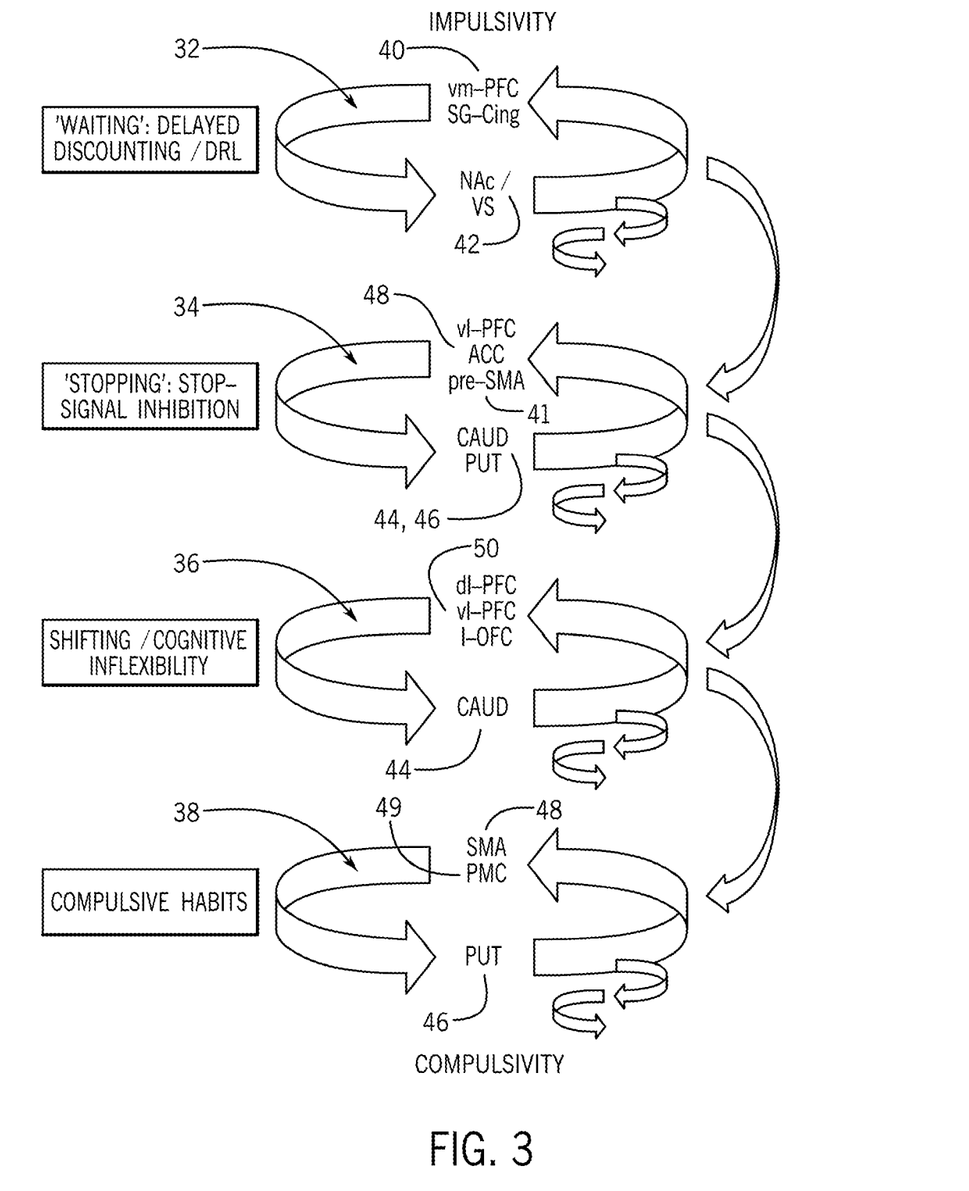
FIG. 3 is a schematic view of the cortico-striato-thalamo-cortical circuits shown in FIGS. 1A-2, from a different perspective illustrating the connections between them.

FIG. 3 shows a set of different CSTC loops 32, 34, 36, 38 believed to be prominent causes of OCD-type symptoms in humans. For example, high connectivity between the prefrontal cortex 40 and the ventral striatum 42 is believed to contribute to impulsive behavior in humans. Connectivity between the caudate nucleus 44 and putamen 46 and the prefrontal cortex 40, ACC 41, SMA 48, and the orbitofrontal cortex 50 is believed to interrupt motor functions and cognitive flexibility. Compulsive behaviors are believed to be the result of looping between the SMA 48, premotor cortex (PMC) 49, and the putamen 46. While normal cognitive function operates using feedback loops such as the circuits 12, 20, 26, 32, 34, 36, 38 shown in FIGS. 1A-4B, patients suffering from mental disorders like OCD and depression often exhibit increased connectivity within the CSTC loops 12, 20, 26, 32, 34, 36, 38. Instead of transferring information out of the loops 12, 20, 26, 32, 34, 36, 38 (e.g., through the thalamus to other locations in the brain 10), signals in the brain 10 get caught in these CSTC loops 12, 20, 26, 32, 34, 36, 38, which can negatively affect behavior, mood, cognitive ability, and motor skills.

Figure 4A:
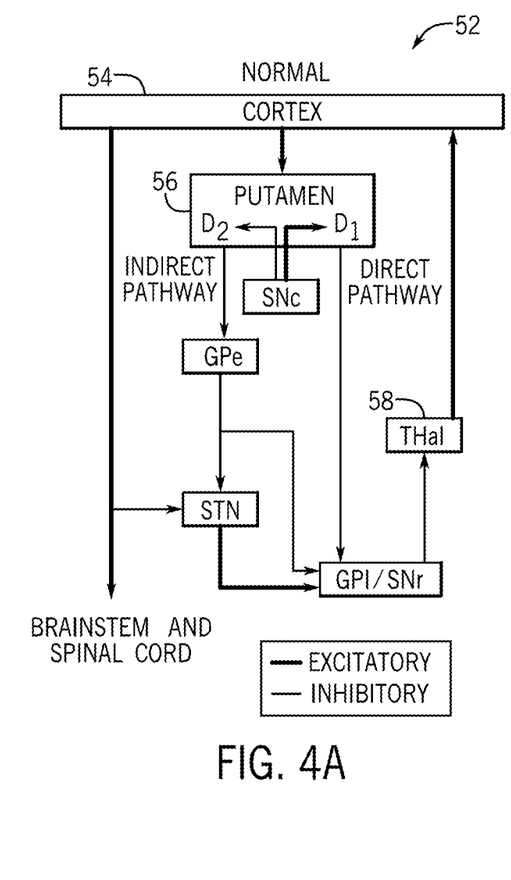
FIG. 4A is a schematic view of an alternate type of recurrent circuit, involved in Parkinson disease, shown in its normal state that causes normal brain function.
Figure 4B:
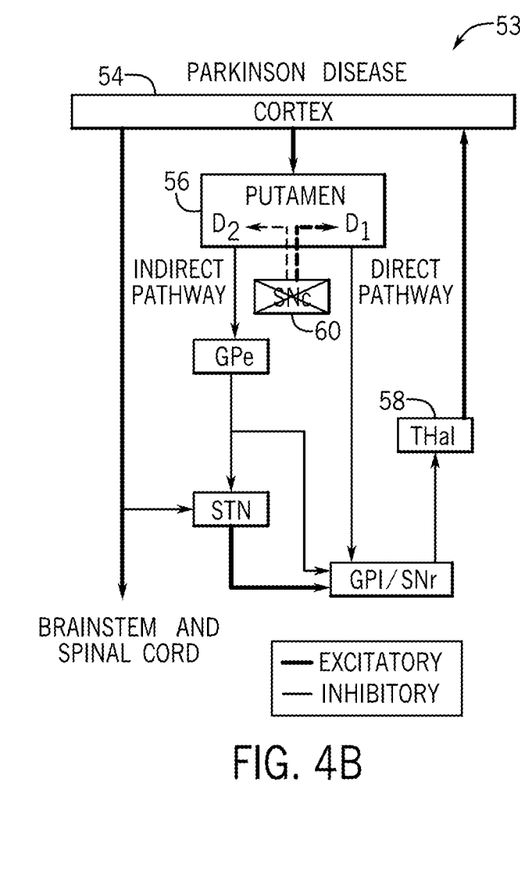
FIG. 4B is a schematic view of the same circuit as 4A, now in a hyper-connected state that would lead to a patient exhibiting Parkinson Disease.

Similar looping in the brain 10 can be attributed to Parkinson Disease, as shown in FIGS. 4A and 4B. FIG. 4A demonstrates normal brain function 52 within an individual, which operates as a loop causing successful motor function. Brain function can originate in the cortex 54, which can then pass through the putamen 56 and eventually to the thalamus 58, where it may again communicate with the cortex 54. Similar to patients suffering OCD, patients suffering from Parkinson Disease (loop 53, FIG. 4B) have exhibited increased connectivity within basal ganglia loops that affects motor function. While some decrease in motor skills may be attributed to deteriorating communication between the putamen 56 and the substantia nigra (SNc) 60, increased connectivity within the basal ganglia loops can cause a person to become motorically stuck, a symptom frequently observed with patients suffering from Parkinson Disease.

Figure 5:
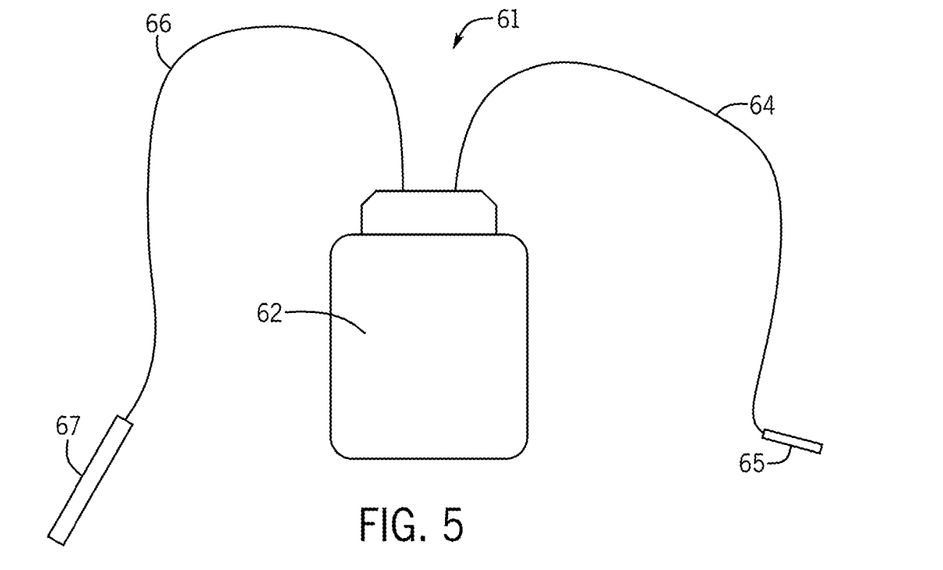
FIG. 5 is a perspective view of a signal generator and electrodes that can be used to elicit disharmony within cortico-striato-thalamo-cortical or similar recurrent circuits within the brain.

Referring to FIG. 5, a system 61 for treating OCD and other mental and neurological disorders is provided. The system includes a signal generator 62, a first electrode 64, and a second electrode 66. In some aspects, the first electrode 64 includes a DBS lead 65, while the second electrode 66 includes a paddle-type electrode 67. For example, the second electrode 66 can be a cortical strip electrode. The first electrode 64 and second electrode 66 are electrically coupled to the signal generator 62, and can transmit signals from the signal generator 62 to the brain 10, for example.

In some aspects, one or both of the first electrode 64 and the second electrode 66 are MRI-safe electrodes that are substantially transparent to radio waves in clinically-applicable magnetic resonance environments. For example, the first electrode 64 could include a lead formed with a structure similar to the MRI leads disclosed and described in U.S. Patent Application 2016/0331960A1, which is hereby incorporated by reference in its entirety. In some non-limiting examples, both the first electrode 64 and the second electrode 66 include DBS leads.

Figure 6:
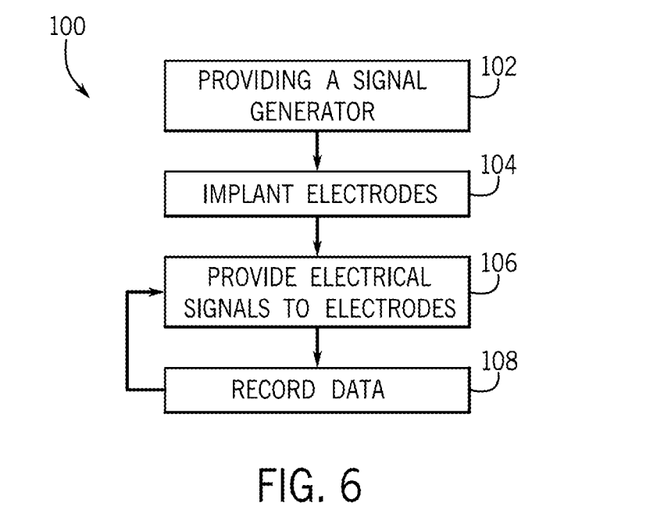
FIG. 6 is a flowchart detailing a method of disrupting the circuits of FIGS. 1A-4B using the signal generator and electrodes of FIG. 5, in accordance with aspects of the disclosure.

Referring to FIG. 6, a method 100 for treating mental disorders associated with high connectivity in circuits using the system 61 in FIG. 5 is illustrated. The method 100 disrupts the connectivity within the brain 10 of a patient, which can alleviate certain obsessive or compulsive thoughts, activities, or actions, and may also provide improved motor skills. The method 100 involves eliciting disharmony in circuits 12, 20, 26, 32, 34, 36, 38 in the brain 10, which can destroy hyper-connectivity within the brain 10 to restore normal feedback looping and communication.

The method 100 can begin by first providing one or more signal generators 62 at step 102. The signal generator(s) 62 can be a Deep Brain Stimulation (DBS) device, for example. The Medtronic Activa® device, Boston Scientific Vercise™ PC, St. Jude Medical Infinity™ DBS system, or other implantable pulse generating devices (IPG's) can be used to provide stimulation to one or both of the electrodes 64, 66. The signal generator 62 can be surgically implanted into a patient (e.g., during step 104, under anesthesia). The signal generator 62 can produce one or more electrical signals, which can be passed through electrodes 64, 66, shown in FIG. 5. In some embodiments, multiple independent chips can be present within the signal generator 62 to produce separate independent signals to each electrode 64, 66. The electrodes 64, 66 can be electrically coupled to the signal generator 62 to transport electrical signals from the signal generator 62 toward an external environment, such as different areas of the brain 10 of a patient.

Figure 7A:
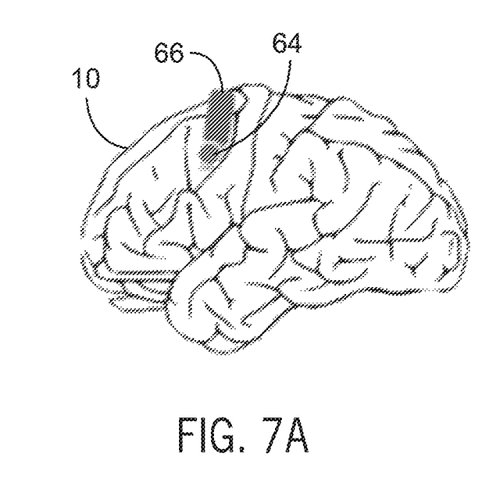
FIG. 7A is a sagittal view of a brain detailing locations where electrodes can be implanted to perform methods in accordance with aspects of the disclosure.
Figure 7B:
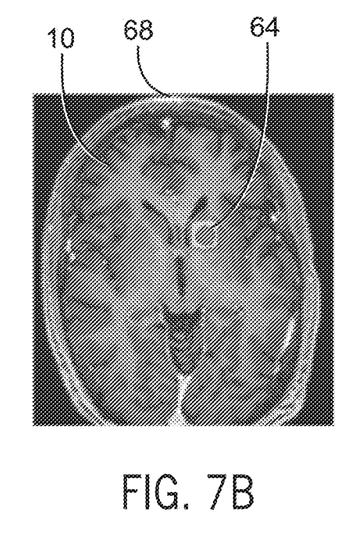
FIG. 7B is an axial view of the brain detailing locations where electrodes can be implanted to perform methods in accordance with aspects of the disclosure.
Figure 7C:
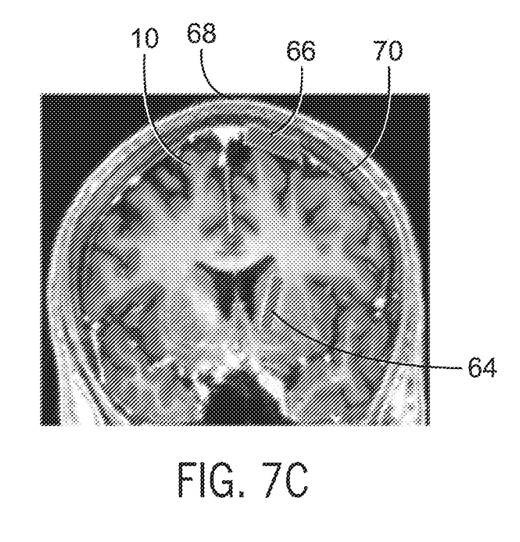
FIG. 7C is a coronal view of the brain detailing locations where electrodes can be implanted to perform methods in accordance with aspects of the disclosure.

The electrodes 64, 66 can then be implanted into the brain 10 of the patient at block 104. As shown in FIGS. 7A-7C, the electrodes 64, 66 can be implanted into two different areas of the brain 10, but within a common circuit (e.g., within the affective circuit 12). In some non-limiting examples, the first electrode 64 is implanted into the brain 10 to target the ventral capsule/ventral striatum (VC/VS) area of the brain 10 and the second electrode 66 is implanted into the brain 10 to target the supplementary motor area (SMA).

Electrode placement at these locations can allow simultaneous striatal and cortical intervention and monitoring of loops, as shown in FIGS. 1A-4B. The SMA is tightly coupled to the ACC 14 shown in the circuit 12 in FIG. 1A. The NAc 16, which partially forms the VC/VS, has been shown to operate within a single CSTC circuit 12 with the ACC 14. Providing electrical signals to the SMA and VC/VS simultaneously creates stimulation at multiple points within the same circuit 12, and can help break pathological synchrony within the brain 10 that can cause mental disorders, such as OCD, Parkinson Disease, depression, or PTSD. In some aspects, one of the electrodes 64, 66 can be directly implanted into the dACC. For example, a second DBS lead can be used to directly stimulate the dACC to disrupt looping.

In some aspects, the step 104 of implanting the electrodes 64, 66 occurs under local anesthesia. A stereotaxic frame can be fitted to the patient, which can allow for precise placement of the electrodes 64, 66 into different areas of the brain 10. The anterior commissure and the posterior commissure can be anesthetized using standard T1-weighted MR images, for example. The internal capsule of the brain 10 can be visualized using an inversion recovery sequence. In some aspects, a coronal T2-weighted MR image can be used to guide the trajectory of the first electrode 64 through the internal capsule in relation to the surrounding striatal structures. Using coordinates individually determined by preoperative MRI images, the first electrode 64 can be inserted into the anterior limb of the internal capsule and fixed to the skull 68. In some aspects, the first electrode 64 includes a tetrapolar lead. Once secured within the patient, the first electrode 64 can stimulate the VC/VS.

The second electrode 66 can be an implanted into the SMA under direct visualization. In some aspects, the first electrode 64 and second electrode 66 are implanted through a common burr hole formed through the skull 68, which can allow direct visualization of dural and bony landmarks overlaying the middle frontal gyms, which corresponds to the dlPFC. Once placed into contact with the SMA, the second electrode 66 can be sutured to dura 70 to anchor it into place. In some aspects, the second electrode 66 can have an epicortical lead. Once the first electrode 64 and second electrode are secured in place, cranioplasty material can be used to cover the burr hole formed through the skull 68. The location of the electrodes can then be confirmed with intra-operative x-ray and post-operative CT scans.

In some aspects, the first electrode 64 and second electrode 66 can be tested prior to anchoring them within the skull 68 of a patient. The electrode testing can include varying voltages, frequencies, and amperages to verify that no adverse effects are experienced by a patient. If adverse effects are reported, the electrodes 64, 66 can be repositioned, and the testing can occur again. If no adverse effects are observed, the electrodes 64, 66 can be sutured or cemented in place. The electrodes 64, 66 can be coupled to the one or more signal generators 62, which can be implanted into the chest of the patient. Extension wires (not shown) can pass from the scalp area to the subclavicular region and can connect each electrode 64, 66 to each subcutaneous signal generator 62. Once the electrodes 64 are electrically coupled to the signal generator(s) 62, a head CT scan can be taken to verify that no postoperative hemorrhaging or infection has occurred as a result of the electrode placement. The CT scan can be coregistered with a preoperative MRI to verify electrode 64, 66 placement accuracy.

Once the electrodes 64, 66 are properly placed within the patient, electrical signals can be passed to the electrodes 64, 66 at step 106. A first electrical signal can be produced by the signal generator 62 and passed to the first electrode 64, while a second electrical signal can be produced by the signal generator 62 and passed to the second electrode 66. As indicated previously, the electrodes 64, 66 are placed at two different locations within a common circuit (e.g., the affective circuit 12, shown in FIG. 1A). To break synchrony within the circuit, the electrodes 64, 66 can be provided with mismatched signals. In some aspects, the frequency of the first electrical signal and the second electrical signal can be unequal. For example, the first electrode 64 can be provided with an electrical signal having a frequency differing from the electrical signal provided to the second electrode 66 by at least 1 Hz.

The parameters of the first electrical signal and the second electrical signal can be selected from a wide range of physiological and non-physiological frequencies. For example, depending upon the mental state of a patient, brain waves between about 2 Hz and about 60 Hz may naturally occur within the brain 10. In some aspects, the first electrical signal is provided with a frequency within the physiological range (e.g., 2-60 Hz), while the second electrical signal is provided with a frequency outside the physiological range to promote disharmony within the same circuit. For example, a naturally occurring frequency within a circuit may be chosen for one of the first and second electrodes 64 and 66, and a mismatched (e.g., at least 1 Hz difference) frequency may be chosen for the other of the first and second electrodes 64 and 66.

In some aspects, the frequency of the first signal and second signal are each below about 30 Hz. For example, the first electrode 64 can be provided with a signal at about 16 Hz while the second electrode 66 is provided with a signal at about 11 Hz. In other aspects, the frequency of the first signal and the second signal can both be greater than about 100 Hz. For example, the first electrical signal can be provided to the first electrode 64 at about 135 Hz, while the second electrode 66 is provided with a second electrical signal at about 130 Hz.

The amplitude and pulse width of the signals can be adjusted as well. In some aspects, a potential of between about 1 and 15 V can be applied to the electrodes 64, 66 to produce electrical signals with amperages between about 1 and about 10 mA. The electrical signals can be pulsed, and can be provided with a pulse width between about 50 μs and about 300 μs. In some aspects, the amplitude and pulse shapes of the electrical signals are approximately equivalent. For example, both the first electrical signal and the second electrical signal can be provided with a pulse width of approximately 150 μs. In some non-limiting examples, a 4 V potential can be applied to the electrodes 64, 66 to produce a 4 mA signal at each of the two unequal frequencies. In other non-limiting examples, other voltage potentials and currents may be applied to the electrodes. The electrical signals can be provided to the electrodes 64, 66 simultaneously, as the difference in frequency prevents the first and second electrical signals from synchronizing or communicating with one another. Each electrical signal can be produced by a separate signal generator 62.

The mismatched frequency of the first electrical signal and the second electrical signal supplied to the first and second electrodes 64 and 66 can break pathological synchrony and connectivity within the CSTC loops. Mismatched stimulation can suppress cortico-striatal coherence and can positively affect mood, behavior, memory, cognition, and impulsivity. The multiple-site stimulation of the cortical and subcortical areas of the brain promotes organization within the brain and can help restore normal communication within the brain, which can help alleviate symptoms associated with OCD and other diseases associated with high connectivity within CSTC circuits.

In some aspects, the method 100 further includes the step of recording data from the electrodes 64, 66 at step 108. For example, the signal generator 62 includes a memory and can also serve as a recording device that receives and records data from the electrodes 64, 66. In some aspects, the signal generator 62 observes the local field potential (LFP) as the signal generator 62 operates. The signal generator 62 can store LFP data and can transmit the data to a remote computer (not shown). In some aspects, the method 100 further includes performing additional testing, such as taking an electroencephalogram (EEG), taking a YBOCS test, Skin Conductance Response (SCR) test, depressive symptoms test, or other types of mental disorder testing.

The step of recording data 108 can also include using the recorded data to adjust parameters within the signal generator 62. For example, the signal generator 62 can include a processor that receives the recorded data 108 to determine that a change to the first electrical signal or the second electrical signal is needed to optimize treatment. In some non-limiting examples, the first electrode 64 and second electrode 66 continuously monitor the LFP at their respective locations within the brain 10, and communicate those results to the signal generator 62. If the processor within the signal generator 62 observes that the LFP has exhibited a value too high or too low, the signal generator can adjust the frequency, pulse width, voltage, amperage, or phase of the first electrical signal or the second electrical signal. The LFP can be continuously monitored with the first electrode 64 and the second electrode 66, and the signal generator 62 can constantly adjust the parameters of the first electrical signal and the second electrical signal to provide closed-loop treatment.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Thus, while the invention has been described in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

We claim:

1. A method of using deep brain stimulation (DBS) for treating mental disorders associated with high connectivity in a brain circuit, the method comprising:
   providing a first electrical signal having a first frequency to a first electrode implanted into a ventral capsule/ventral striatum (VC/VS) within a brain circuit; and
   providing a second electrical signal having a second frequency to a second electrode implanted directly at, or in a region coupled to, a dorsal anterior cingulate cortex (dACC) within the brain circuit, the first frequency and the second frequency being unequal,
   wherein the first and second frequencies are selected to elicit disharmony that reduces coherence within the brain circuit.

2. The method of claim 1, wherein the second electrode is implanted into a supplementary motor area (SMA).

3. The method of claim 1, wherein the method further comprises recording brain activity using a recording device coupled to the first electrode and the second electrode.

4. The method of claim 3, wherein the step of recording brain activity using the recording device further includes measuring local field potential (LFP) at least one of the first electrode and the second electrode.

5. The method of claim 1, wherein the method further includes the step of performing an electroencephalogram (EEG).

6. The method of claim 1, wherein the first frequency and the second frequency differ from one another by more than about one Hertz.

7. The method of claim 1, wherein one of the first frequency is greater than about 100 Hertz or the second frequency is greater than about 100 Hertz.

8. The method of claim 1, wherein one of the first electrode and the second electrode is either a paddle-type electrode or a cortical strip electrode.

9. The method of claim 1, wherein the step of providing the first electrical signal to the first electrode and the step of providing the second electrical signal to the second electrode are each performed using an implantable pulse generator (IPG).

10. The method of claim 1, wherein the first frequency and the second frequency are less than about 30 Hertz.

11. The method of claim 10, wherein the first frequency is about 16 Hertz and the second frequency is about 11 Hertz.

12. An apparatus for treating mental and neurological disorders involving high brain connectivity, the apparatus comprising:
a first electrode configured to be placed within a ventral capsule/ventral striatum (VC/VS) within a cortico-striato-thalamo-cortical (CSTC) brain circuit;
a second electrode configured to be placed directly within, or in a region coupled to, a dorsal anterior cingulate cortex (dACC) within the CSTC brain circuit; and
a signal generator electrically coupled to the first electrode and the second electrode, the signal generator configured to:
generate a first signal at a first frequency and communicate the first signal to the first electrode,
generate a second signal at a second frequency and communicate the second signal to the second electrode, the first frequency and the second frequency differing by at least about one Hertz,
wherein the first and second frequencies are selected to elicit disharmony that reduces coherence within the CSTC brain circuit.

13. The apparatus of claim 12, further comprising a recording device coupled to the signal generator to receive and record electrical activity in the CSTC circuit.

14. The apparatus of claim 12, wherein the first frequency differs from the second frequency by about five Hertz.

15. The apparatus of claim 12, wherein the first frequency is about 130 Hertz and the second frequency is about 135 Hertz.

16. A method of disrupting circuits within a brain using deep brain stimulation (DBS), the method comprising:
providing a first electrical signal to a first electrode and a second electrical signal to a second electrode, the first electrode positioned at a ventral capsule/ventral striatum (VC/VS) and the second electrode positioned directly in, or in a region coupled to, a dorsal anterior cingulate cortex (dACC), such that the first and second electrodes are within a common brain circuit, the first and second electrical signals having mismatched frequencies,
wherein the mismatched frequencies are selected to elicit disharmony that reduces coherence within the brain circuit.

17. The method of claim 16, wherein the mismatched frequencies of the first electrical signal and the second electrical signal differ by at least one Hertz.

18. The method of claim 16, wherein the second electrode is positioned in a supplementary motor area (SMA) of the brain.

19. The method of claim 16, wherein one of a first voltage is used to produce the first electrical signal, with the first voltage being between about 1 Volt and about 15 Volts, or
the first electrical signal and the second electrical signal have a pulse width between about 50 ns and about 300 µs.

20. The method of claim 16, wherein the method further comprises adjusting a parameter of the first electrical signal or the second electrical signal based upon electrical activity measured by the first electrode and the second electrode, and wherein the parameter of the first electrical signal or the second electrical signal that is adjusted includes at least one of a frequency, a voltage, an amperage, a pulse width, or a phase.

* * * * *

UNITED STATES PATENT AND TRADEMARK OFFICE
CERTIFICATE OF CORRECTION

PATENT NO.       : 11,400,292 B2
APPLICATION NO.  : 16/468134
DATED            : August 2, 2022
INVENTOR(S)      : Emad N. Eskandar et al.

It is certified that error appears in the above-identified patent and that said Letters Patent is hereby corrected as shown below:

In the Specification

Column 6, Line 27, "gyms" should be --gyrus--.

Signed and Sealed this
Eleventh Day of October, 2022

Katherine Kelly Vidal
*Director of the United States Patent and Trademark Office*